(12) United States Patent
Salzburger et al.

(10) Patent No.: US 7,395,715 B2
(45) Date of Patent: Jul. 8, 2008

(54) ELECTROMAGNETIC ULTRASOUND PROBE

(75) Inventors: Hans-Jürgen Salzburger, Neunkirchen (DE); Alexander Viskov, Saarbrücken (DE)

(73) Assignee: Fraunhofer-Gesellschaft zur Förderung der Angewandten Forschung e.V., Munich (DE)

( * ) Notice: Subject to any disclaimer, the term of this patent is extended or adjusted under 35 U.S.C. 154(b) by 100 days.

(21) Appl. No.: 10/539,438

(22) PCT Filed: Dec. 6, 2003

(86) PCT No.: PCT/EP03/13856

§ 371 (c)(1),
(2), (4) Date: Mar. 30, 2006

(87) PCT Pub. No.: WO2004/056498

PCT Pub. Date: Jul. 8, 2004

(65) Prior Publication Data

US 2006/0236764 A1 Oct. 26, 2006

(30) Foreign Application Priority Data

Dec. 19, 2002 (DE) ............................ 102 59 409

(51) Int. Cl.
*G01N 29/24* (2006.01)
(52) U.S. Cl. ........................................... 73/643
(58) Field of Classification Search .................. 73/643
See application file for complete search history.

(56) References Cited

U.S. PATENT DOCUMENTS 6,009,756 A * 1/2000 Willems et al. ............... 73/643

FOREIGN PATENT DOCUMENTS

DE 36 37 366 A1 5/1988

(Continued)

OTHER PUBLICATIONS

Petersen, G. L. et al, "Resonance Techniques and Apparatus for Elastic-Wave Velocity Determined in Thin Metal Plates," Review of Scientific Instruments, American Institute of Physics. New York, U.S. vol. 65, No. 1, 1994, pp. 192-198.

* cited by examiner

*Primary Examiner*—John E Chapman
(74) *Attorney, Agent, or Firm*—Antonelli, Terry, Stout & Kraus, LLP.

(57) ABSTRACT

Disclosed is an electromagnetic ultrasonic probe for coupling-media-free generation and reception of ultrasonic waves in the form of linearly polarized transverse waves in a workpiece (5), and from a workpiece (5), having a unit which generates the ultrasonic waves inside the workpiece (5) and which is provided with a transmission coil arrangement (7), to which a high-frequency voltage can be applied to generate a high-frequency magnetic field, and a premagnetizing unit (V) to generate a quasi-static magnetic field superimposed on the high-frequency magnetic field in the workpiece (5), and an ultrasonic waves reception unit providing a reception coil arrangement (8), with the transmission coil arrangement (7) and the reception coil arrangement (8) being disposed torus-shaped at least on one partially toroidally designed magnetic core (6), which is provided with two front ends (11) which can be turned to face the workpiece (5) and via which the high-frequency magnetic fields can be coupled into, respectively coupled out of, the workpiece (5). The premagnetizing unit (V) is contactable directly or indirectly with the workpiece (5) through a contact area (9) and by the at least one partially toroidally-shaped magnetic core (6) is disposed laterally next to the contact area (9) of the premagnetizing unit (V) so that the premagnetizing unit (V) can project over the partially toroidally designed magnetic core (6) perpendicular to the contact area (9).

14 Claims, 2 Drawing Sheets

FOREIGN PATENT DOCUMENTS

| | | |
|---|---|---|
| DE | 39 35 432 A1 | 4/1991 |
| DE | 195 49 207 A1 | 7/1997 |
| EP | 0 440 317 A1 | 8/1991 |
| EP | 0 579 255 B1 | 1/1994 |

ELECTROMAGNETIC ULTRASOUND PROBE

BACKGROUND OF THE INVENTION

The present invention relates to an electromagnetic ultrasonic probe for coupling media-free generation and reception of ultrasonic waves in the form of linearly polarized transverse waves in a workpiece, and therefrom. Such a type ultrasonic probe provides a unit which generates ultrasonic waves inside the workpiece having a transmission coil arrangement to which a high-frequency voltage can be applied to generate a high-frequency field. A premagnetizing unit ensures generation of a quasi-static magnetic field superimposed on the high-frequency magnetic field in the workpiece. Furthermore, to detect ultrasonic waves, a unit is provided to receive the ultrasonic waves. The ultrasonic reception unit is provided with a reception coil arrangement which can be connected to an evaluation unit.

In order to prevent the filigree transmission coil and reception coil arrangements from suffering mechanical damage due to direct contact with the surface of the workpiece, the arrangements are torus-shaped on at least one partially toroidally magnetic core, which is provided with at least two front ends that can be turned to face the workpiece. The high-frequency magnetic fields can be coupled into, and out of, the workpiece via these two front ends, permitting in this manner the coil arrangements to be disposed on the surface of the workpiece at a distance from each other. Nonetheless the high-frequency magnetic fields required for the generation and detection of ultrasonic waves inside the workpiece are effectively coupled into, and out of, the workpiece via a partially toroidal-shaped magnetic core.

Such ultrasonic probes permit generation and reception of linear polarized transverse waves which are irradiated perpendicularly under the probe into the workpiece, and are received from this direction and oscillate perpendicular to their propagation direction in a plane. Technical fields of application of such ultrasonic probes are, for example, non-destructive examination of electrically conductive workpieces for material flaws, such as cracks, in particular perpendicular to the polarization direction of the ultrasonic waves and crack-like flaws that are oriented parallel to the propagation direction, including other processes based on ultrasonic velocity and polarization, such as for example measuring voltage or, in particular, measuring thickness.

DESCRIPTION OF THE PRIOR ART

The prior art coupling-media-free electromagnetic probes convert electromagnetic field energies into elastic energy of an ultrasonic wave and inversely. The conversion mechanism is based on the interaction between the electromagnetic field and an electrically conducting material in which a static magnetic field or a quasi-static magnetic field applied from the outside passes through the workpiece. The term "quasi-static" magnetic field comprises, in addition to the actual static magnetic field, which for example can be generated by means of permanent magnets or low-frequency magnetic fields which have an alternating frequency which is much lower than the high frequency with which the transmission coil arrangement is operated to generate high-frequency fields.

In order to excite ultrasonic waves inside an electrically conducting workpiece, at least one part of the high-frequency magnetic field, whose frequency range lies within the ultrasonic frequency range, and which is generated by the high-frequency coil arrangement, is coupled into the workpiece. Eddy currents are induced at skin depth which in conjunction with the "quasi-static" magnetic field generate ultrasonic waves due to the Lorentz forces or magnetostrictions occurring inside the workpiece.

Detection of ultrasonic waves occurring inside the workpiece occurs inversely by detection of the electric voltage induced in the reception coil arrangement resulting from high-frequency fields. The high frequency fields are generated by the flow of electrical charges, due to the ultrasonic waves, in the workpiece inside the "quasi-static" magnetic field.

Prior art electromagnetic ultrasonic transducers are based on the common goal of optimizing measuring sensitivity and, related thereto, optimizing the signal amplitudes that can be produced by the transmission coil and the reception coil arrangements in the transmission signal and in the reception signal. The objective, on the one hand, is to design, as loss free as possible, the coupling mechanism by which the generated and to-be-detected high-frequency fields are coupled between the ultrasonic transducer and the workpiece and, on the other hand, to select the field strength of the quasi-static magnetic field to be as large as possible, which is significant for generating and detecting ultrasonic waves.

DE 42 23 470 C2 describes a generic electromagnetic probe for vertical acoustic irradiation of linearly polarized transverse waves, in which the high-frequency magnetic fields are coupled in and out in a most efficient manner between the probe and the workpiece without, as is the case with many other probes, placing the transmission and reception coils, usually designed as high-frequency air coils, directly on the surface of the workpiece. But the prior art electromagnetic probe of FIG. 2, which is described in this printed publication, is provided with a half-open toroidal core 6, made commercially of amorphous material, around which a transmission coil arrangement 7 and a reception coil arrangement 8, are wound. The front ends 11 of the half-open toroidal tape core 6 act as coupling areas for the high-frequency magnetic fields and can be placed in a suitable manner on the surface of the workpiece 5 to be examined. The high-frequency magnetic fields generated by the high-frequency transmission coil arrangement 7 reach via the front ends 11 of the toroidal core 6 into the workpiece 5 and are able to induce close-to-the surface eddy currents 12 at skin depth inside the workpiece 5.

The quasi-static magnetic field oriented perpendicular to the surface of the workpiece 5 required for sound conversion is generated by means of two permanent magnets 3 of the same polarity and is conveyed to the material surface of the workpiece 5 via a soft iron core 2 provided inside the toroidal core. The premagnetizing unit required for producing the "quasi-static" magnetic field that is oriented perpendicular to the surface of the workpiece is located inside the open part of the toroidal core 1.

A drawback of the aforedescribed embodiment of a prior art electromagnetic probe is that only low signal strengths are obtainable with this probe for generating and detecting ultrasonic waves. Thus the construction-based low signal strength of the premagnetizing unit prevents generating high magnetic fluxes.

In addition to the preceding printed publication, DE 36 37 366 A1 and DE 195 49 207 A1 describe probes for nondestructive examination. However, the construction of these probes differs from the previously described probes. For instance, DE 36 37 366 A1 discloses an electromagnetic ultrasonic transducer, whose high-frequency transmission and reception coil arrangement are placed along a rib-like carrier structure over which a magnetic arrangement for generating the quasi-static magnetic field projects. DE 195 49 207 A1 describes a corresponding probe which is provided with a magnetic field concentrating element but differs in all other details from the device described in the introduction.

SUMMARY OF THE INVENTION

The present invention provides an electromagnetic ultrasonic probe which generates linearly polarized transverse waves inside a workpiece with the probe have higher signal amplitudes than with prior art probes. In particular, detection sensitivity of a probe in accordance with the invention should be increased without having to place the high-frequency coil arrangements required for generating and receiving the ultrasonic waves near to the surface of the workpiece.

The present invention is based on providing a selective increase in the construction volume of the premagnetizing unit required for the "quasi-static magnetic field" based on the electromagnetic probe of DE 42 23 470 C2. Enlarging the premagnetizing unit permits increasing the strength of the "quasi-static" magnetic field entering the workpiece perpendicular thereto in such a manner that the Lorentz forces or the magnetostrictions responsible for generating ultrasonic waves inside the workpiece are increased, which ultimately causes ultrasonic waves of greater amplitude.

Inversely, the magnetic field enhancement of the "quasi-static" magnetic field, as a result of the construction of the invention, entering the workpiece results in the formation of stronger high-frequency fields which are generated by ultrasonic-wave-based electrical charge flow inside the workpieces in the presence of quasi-static magnetic fields and are coupled into the toroidal core via the front ends. These high-frequency fields enable inducing higher electrical voltages into the reception coil arrangement, by means of which the detection sensitivity of the electromagnetic ultrasonic transducer can be improved considerably.

A key element of the invention is that an electromagnetic ultrasonic probe provides a premagnetizing unit which can be contacted directly or indirectly with the workpiece via a contact area. The premagnetizing unit is disposed laterally beside the at least one partially toroidally-shaped magnetic core, preferably shaped in the form of a toroidal core, in such a manner that the premagnetizing unit is able to project over the partially toroidally-shaped magnetic core in a manner perpendicular to the contact area.

Contrary to the aforecited DE 42 23 470 C2, the preferably half open toroidal core, due to the arrangement, does not project over the premagnetizing unit, but rather the toroidal tape core is located laterally directly beside the premagnetizing unit without projecting over the premagnetizing unit or only just parts of it projection to the surface of the workpiece.

In a preferred embodiment, the partially toroidally-shaped magnetic core, built as a toroidal core, is inclined with regard to toroidal plane thereof at an angle $\alpha$ to the contact area, with the two front ends of the toroidal core facing the workpiece also forming an angle $\alpha$ with the toroidal plane in such a manner that the toroidal core lies largely flush with the front ends on the workpiece. The incline of the toroidal plane of the toroidal core is preferably formed to the contact area so that the high-frequency magnetic fields, that can be coupled into the workpiece via the front ends, extend into the region under the contact area between the premagnetizing unit and the workpiece and in this way interact with the quasi-static magnetic field inside the workpiece to generate eddy currents.

The lateral arrangement of at least one partially toroidal magnetic core relative to the contact area between the premagnetizing unit and the workpiece permits constructing the premagnetizing unit, for example in the form of one permanent magnet or a multiplicity of permanent magnets, as large as desired, in a particular vertical extension to the contact area in order to generate a desired strong "quasi static" magnetic field. Dimensioning of the premagnetizing unit is unlimited due to the fact that the ultrasonic transducer arrangement is open upward perpendicular to the contact area. Only handling aspects can limit the size.

Based on the arrangement of an electromagnetic ultrasonic transducer known from DE 42 23 470 C2, a simple embodiment provides for the use of a single toroidal core along which both a high-frequency coil arrangement for a transmission unit and a reception unit are wound.

One preferred embodiment, however, provides for two partially toroidally-shaped magnetic core constructed as toroidal cores disposed on opposite sides with regard to the contact area and thus relative to the premagnetizing unit. Due to separate signal and in order to prevent mutual interference of the transmission signals and the reception signals, the transmission coil arrangement and the reception coil arrangement are separated from each other on the toroidal cores located opposite the premagnetizing unit. Such a separated coil arrangement on two separate toroidal cores primarily contributes to reducing so-called dead times which occur if the transmission coil arrangement and the reception coil arrangement are disposed on the same toroidal core. Ultimately this leads to the toroidal core being unable to detect reception signals during the short time periods in which the transmission coil arrangement conveys the toroidal core into saturation magnetization. If the ultrasonic transducer is utilized, for example for measuring thickness, these saturation effects lead to the occurrence of dead times which are not accessible for measuring thickness. This is due to the temporally immediate succession of transmission signals and reception signals, the reception signals can, due to the saturation effect be detected only following a minimum interval after the transmission signal. Therefore, workpieces must have at least a thickness of 3-4 mm to be measured.

In a further preferred embodiment, the arrangement is provided with two pairs of toroidal cores disposed orthogonally in relation to each other about the contact area, which preferably is rectangular in shape. In this manner, two linearly polarized transverse wave fields can be generated inside a workpiece with oscillation planes that are oriented perpendicular to each other. In this manner, material flaws, for example in the form of cracks which are oriented either perpendicular to one or the other oscillation plane, are precisely detected.

For an efficient as possible coupling, that is low loss, and concentrated coupling-in of the "quasi-static" magnetic field into the to-be-examined workpiece, a preferred embodiment utilizes two identical polarity permanent magnets which are both at least partially enclosed by a block made of a soft magnetic material. Connected to the block in direction of the workpiece is a concentrator, which, for its part, also contains a soft magnetic material in order to concentrate the magnetic flux on the contact area. The concentrator itself is provided with two different sized surfaces opposite each other. The larger surface of the two surfaces is connected to the soft magnetic material workpiece which at least partially encloses the permanent magnets with the smaller surface facing the workpiece to-be-examined, which defines the contact area between the premagnetizing unit and the material. As mentioned in the preceding, the contact area is preferably rectangular in shape and along its at least two opposite lateral edges are disposed the toroidal cores which are inclined obliquely to the contact area.

In order to prevent disturbing eddy currents from coupling into the workpiece due to the generated high-frequency fields inside the concentrator as a result of the proximity to the toroidal cores conducting the high-frequency fields, the concentrator, instead of being composed of a homogeneous electrically conducting material, is composed of an electrically nonconducting material into which ferromagnetic particles are introduced in a matrix in order to conduct and to concentrate the magnetic flux or the concentrator is constructed like the magnetic core of a transformer and comprises a multiplicity of stacked metal plates.

BRIEF DESCRIPTION OF THE DRAWINGS

The present invention is made more apparent in the following using preferred embodiments with reference to the accompanying drawings without the intention of limiting the scope or spirit of the overall inventive idea.

DETAILED DESCRIPTION OF THE INVENTION

Figure 1:
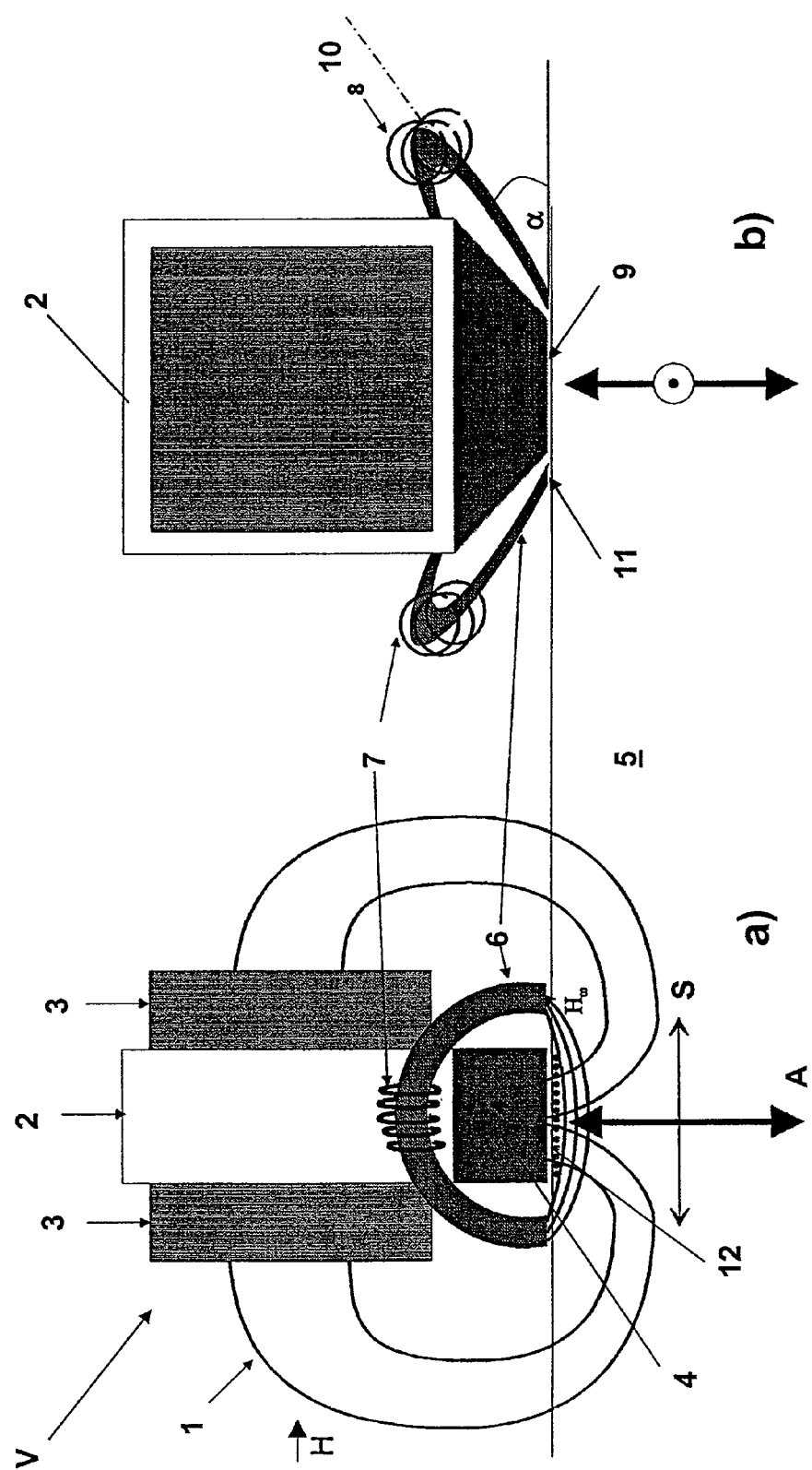
FIGS. 1a,b show a lateral and a front view of an electromagnetic ultrasonic transducer according to the present invention.
Figure 2:
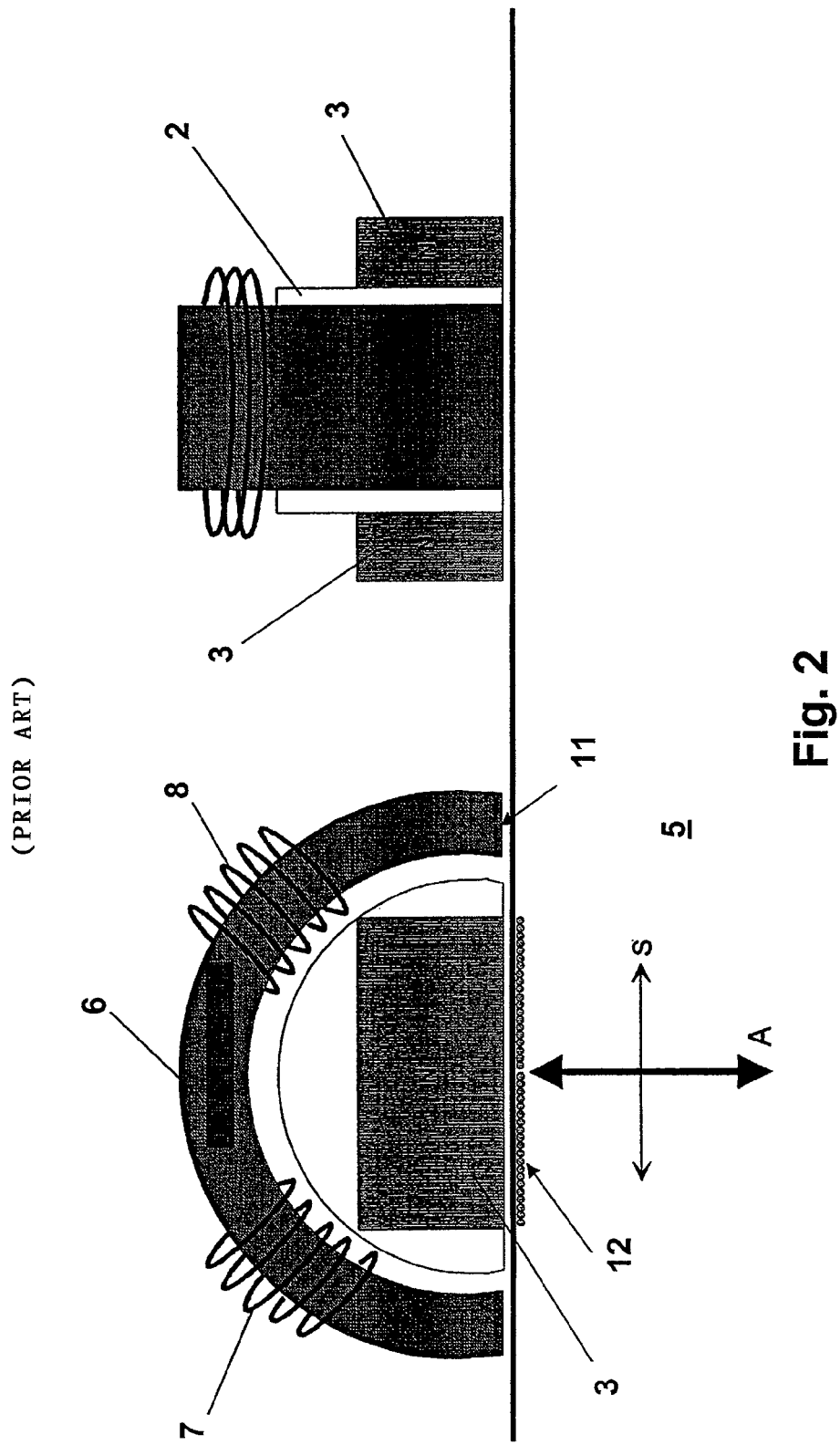
FIG. 2 shows a state-of-the-art electromagnetic transducer.

FIGS. 1a and b show a lateral and a front view of a preferred embodiment of an electromagnetic ultrasonic transducer in accordance with the present invention comprising a premagnetizing unit V for generating a sufficiently strong static magnetic field 1 which enters the material to-be-examined W in a perpendicular manner. The premagnetizing unit V is provided with two permanent magnets 3 of the same polarity which are at least partially enclosed by a soft magnetic material 2, via which the magnetic flux H is introduced into the workpiece 5 perpendicular to its surface via a concentrator 4, which is connected to the material 2.

The front view of FIG. 1 shows that the concentrator 4 with a tapered shape tapering toward the contact area 9 between the premagnetizing unit V and the surface of the workpiece, due to which the magnetic flux H conducted inside the concentrator 4 is concentrated on the narrowly confined contact area 9.

A half open toroidal core 6 is disposed to the left and to the right of the sides of the concentrator 4. The transmission coil arrangement 7 is placed on one of the toroidal cores 6 and the reception coil arrangement 8 on the other core. The toroidal cores 6 are inclined toward the contact area 9 with regard to their partially toroidal planes 10 in such a manner that, on the one hand, it is ensured that the premagnetizing unit V can assume any desired construction height perpendicular to the contact area that projects over the toroidal tape core and, on the other hand, the coil arrangements 7 and 8 are positioned at a distance from the workpiece surface, due to which they are not subject to any mechanical wear as a result of direct contact with the surface of the workpiece 5.

In order to ensure that the high-frequency magnetic fields can be coupled in from, and to, the individual high-frequency coil arrangements 7 and 8 largely with no losses into the workpiece 5 via the surface of the workpiece, the front ends 11 of the toroidal tape cores 6 form with the respective partially toroidal plane 10 an angle $\alpha$ as well, which can fundamentally be selected between 0° and 90°, preferably however is between 30° and 60°. In this manner it is ensured that, despite the inclined position of the toroidal cores 6, the front ends 11 lie flush to the sides of the contact area 9 on the surface of the workpiece 5, permitting coupling in and out of the high-frequency magnetic fields largely without losses.

To trigger the ultrasonic waves, the transmission coil arrangement 7, which is usually connected to a high-frequency generator, is fed a high-frequency current burst signal. The magnetic alternative flux $H_w$ generated by the transmission coil arrangement 7 is coupled into the workpiece 5 via the toroidal core 6 and via a small air gap enclosed between the front ends 11 and the surface of the workpiece 5. A spatially homogenous magnetic alternating field $H_w$ forms at skin depth in the workpiece between the front ends 11 of the toroidal tape core bearing the transmission coil arrangement 7. The eddy currents coupled with the magnetic alternating field $H_w$ inside the workpiece 5 are superimposed on the magnetic field entering the workpiece 5 perpendicularly via the concentrator 4, thereby generating, due to the forming of Lorentz forces and magnetostricitions, ultrasonic waves oscillating perpendicular to the direction of the eddy currents and propagating perpendicular to the surface of the workpiece, and to the contact area 9. The arrow representations indicate the oscillation direction S and the propagation direction A.

The reception mechanism for detecting the ultrasonic waves propagating inside the workpiece is based on the inverse effect, notably the sound velocity developing inside the workpiece of the ultrasonic wave returning to the probe, in interaction with the static magnetic field, generates an electrical field, which conducted via the toroidal tape core 6 to the reception coil arrangement 8 induces an electrical voltage therein. The electrical voltage induced in the reception coil arrangement 8 can usually be amplified with a downstream amplifier and correspondingly evaluated with an evaluation unit.

Thus the electromagnetic ultrasonic transducer designed according to the present invention combines the advantages relating to loss-free as possible coupling into and out of high-frequency magnetic fields and detection, into, and out of, the workpiece to-be-examined. For this purpose, the coil arrangements required for generation and reception are disposed at a distance from the surface of the workpiece in an advantageous manner so that they are not subject to any mechanical wear. Moreover, the arrangement in accordance with the present invention offers almost any desired dimensioning of the premagnetizing unit in order to optimize the magnetic field strength of the "quasi-static" magnetic field as desired. This measure ultimately leads to generating greater signal amplitudes for producing stronger ultrasonic waves inside the workpiece, thereby permitting decisively improving the detection sensitivity of the electromagnetic ultrasonic transducer. Dimensioning of the premagnetizing unit is only limited by handling concerns.

LIST OF REFERENCES

1 "quasi-static" magnetic field
2 soft magnetic material
3 permanent magnets
4 concentrator
5 workpiece
6 toroidal core
7 transmission coil arrangement
8 reception coil arrangement
9 contact area
10 partially toroidal plane
11 front end
12 eddy current
S oscillation direction
V premagnetizing unit
A propagation direction

What is claimed is:

1. An electromagnetic ultrasonic probe for coupling-media-free generation and reception of ultrasonic waves in the form of linearly polarized transverse waves in a workpiece, and from the workpiece, comprising:
    a unit for generating the ultrasonic waves inside the workpiece, the unit comprising a transmission coil, to which a high-frequency voltage can be applied to generate a high-frequency magnetic field, and a premagnetizing unit for generating a quasi-static magnetic field superimposed on the high-frequency magnetic field in the workpiece;
    an ultrasonic waves reception unit comprising a reception coil;
    the transmission coil and the reception coil being torus-shaped and being disposed at least on one partially toroidal-shaped magnetic core, having two front ends which can be turned to face the workpiece and through which the high-frequency magnetic fields can be coupled into and coupled out of, the workpiece;
    a contact area for providing direct or indirect contact between the premagnetizing unit and the workpiece through the contact area; and
    the at least one partially toroidal-shaped magnetic core is disposed laterally next to the contact area so that the premagnetizing unit can project over the partially toroidal-shaped magnetic core perpendicular to the contact area.

2. The electromagnetic ultrasonic probe according to claim 1, wherein the premagnetizing unit generates a quasi-static magnetic field with magnetic field lines passing through the contact area largely perpendicular thereto.

3. The electromagnetic ultrasonic probe according to claim 1, wherein the premagnetizing unit includes at least one permanent magnet with magnetic field lines which are concentrated by a concentrator on the contact area.

4. The electromagnetic ultrasonic probe according to claim 3, wherein the at least one permanent magnet is at least partly enclosed by a magnetic workpiece which couples the magnetic field lines to the concentrator.

5. The electromagnetic ultrasonic probe according to claim 4, wherein the concentrator comprises a soft magnetic material and has two surfaces opposite each other, one surface being larger than the other surface and the surface which is smaller determining the size of the contact area and the larger surface being connected to the soft magnetic workpiece.

6. The electromagnetic ultrasonic probe according to claim 5, wherein the concentrator comprises an electrically nonconducting material in which ferromagnetic particles are embedded in a matrix, or the concentrator comprises a stack of single metal plates.

7. The electromagnetic ultrasonic probe according to claim 3, wherein the concentrator comprises a magnetic material and has two surfaces opposite each other, one surface being larger than the other surface and the surface which is smaller determining a size of the contact area and the larger surface being connected to the magnetic workpiece.

8. The electromagnetic ultrasonic probe according to claim 7, wherein the concentrator comprises an electrically nonconducting material in which ferromagnetic particles are embedded in a matrix, or the concentrator comprises a stack of single metal plates.

9. The electromagnetic ultrasonic probe according to claim 3, wherein the premagnetizing unit comprises two permanent magnets.

10. The electromagnetic ultrasonic probe according to claim 1, wherein the at least one partially toroidal-shaped magnetic core has a partially toroidal plane forming with the contact area an angle α with 0°<α<90°, and the front ends form the angle α with the partially toroidal plane.

11. The electromagnetic ultrasonic probe according to claim 10, wherein 30°<α<60°.

12. The electromagnetic ultrasonic probe according to claim 1, comprising at least two partially toroidal-shaped magnetic cores, core comprising the transmission coil and the other core comprising the reception coil, and the partially toroidal-shaped magnetic cores are disposed on opposite sides relative to the premagnetizing unit.

13. The electromagnetic ultrasonic probe according to claim 12, wherein the partially toroidal-shaped magnetic cores are axially symmetrical to a axis passing through the premagnetizing unit, and wherein the partially toroidal planes of the partially toroidal-shaped magnetic cores each form an angle with the contact area.

14. The electromagnetic ultrasonic probe according to claim 1, wherein the at least one partially toroidal-shaped magnetic core comprises a toroidal core.

* * * * *